(12) United States Patent
Axelrod et al.

(10) Patent No.: US 7,519,407 B2
(45) Date of Patent: Apr. 14, 2009

(54) OPTICAL SENSING CATHETER SYSTEM

(75) Inventors: Noel Axelrod, Jerusalem (IL); Eran Ofek, Modi'in (IL); Asaf Peleg, Zoran (IL)

(73) Assignee: Physical Logic AG, Zug (CH)

( * ) Notice: Subject to any disclaimer, the term of this patent is extended or adjusted under 35 U.S.C. 154(b) by 62 days.

(21) Appl. No.: 11/678,613

(22) Filed: Feb. 25, 2007

(65) Prior Publication Data

US 2007/0203414 A1    Aug. 30, 2007

Related U.S. Application Data

(60) Provisional application No. 60/777,715, filed on Feb. 28, 2006, provisional application No. 60/777,727, filed on Feb. 28, 2006, provisional application No. 60/775,531, filed on Feb. 21, 2006.

(51) Int. Cl.
   *A61B 5/1455* (2006.01)
   *G02B 6/00* (2006.01)

(52) U.S. Cl. .................... 600/341; 600/342; 385/12

(58) Field of Classification Search ............. 600/310, 600/322, 323, 341, 342; 385/12, 13
   See application file for complete search history.

(56) References Cited

U.S. PATENT DOCUMENTS

| | | | |
|---|---|---|---|
| 4,730,622 A * | 3/1988 | Cohen .................. 600/480 |
| 4,818,710 A | 4/1989 | Sutherland et al. |
| 5,020,537 A | 6/1991 | Gunther |
| 5,048,524 A | 9/1991 | Bailey |
| 5,058,587 A | 10/1991 | Kohno |
| 5,124,130 A * | 6/1992 | Costello et al. .......... 422/82.06 |
| 5,166,990 A * | 11/1992 | Riccitelli et al. ............ 600/342 |
| 5,178,153 A | 1/1993 | Einzig |
| 5,280,786 A | 1/1994 | Wlodarczyk |
| 5,353,792 A * | 10/1994 | Lubbers et al. ............. 600/311 |
| 5,396,350 A | 3/1995 | Beeson et al. |
| 5,425,115 A | 6/1995 | Wagner |
| 5,677,196 A | 10/1997 | Herron et al. |
| 5,790,727 A | 8/1998 | Dhadwal et al. |
| 6,052,220 A | 4/2000 | Lawrence et al. |
| 6,259,841 B1 | 7/2001 | Bhagavatula |

(Continued)

FOREIGN PATENT DOCUMENTS

WO    2004007012 A2    1/2004

(Continued)

OTHER PUBLICATIONS

Friebel M , Meinke M., "Determination of the complex refractive index of highly concentrated hemoglobin solutions using transmittance and reflectance measurements", Journal of Biomedical Optics , vol. 10, Issue 6, 064019 (2005).

(Continued)

*Primary Examiner*—Eric F Winakur
(74) *Attorney, Agent, or Firm*—Edward S. Sherman

(57) ABSTRACT

An optical sensing catheter system for physiological measurements of vascular or arterial parameters at plurality of location deploys wavelength division multiplexing in a common optical fiber to communicate with each optical sensor. The sensors are preferably passive planar waveguide type devices disposed to interact with the environment external to the catheter or other medical device.

14 Claims, 4 Drawing Sheets

Cross Section

U.S. PATENT DOCUMENTS

| | | | |
|---|---|---|---|
| 6,584,335 B1 * | 6/2003 | Haar et al. | 600/322 |
| 6,616,611 B1 | 9/2003 | Moehring | |
| 6,624,061 B2 | 9/2003 | Aoki | |
| 6,704,590 B2 | 3/2004 | Haldeman | |
| 6,859,658 B1 | 2/2005 | Krug | |
| 7,128,713 B2 | 10/2006 | Moehring | |
| 7,164,948 B2 | 1/2007 | Struble | |
| 7,209,605 B2 * | 4/2007 | Cantin et al. | 385/12 |
| 2005/0119543 A1 | 6/2005 | Parker | |

FOREIGN PATENT DOCUMENTS

| | | |
|---|---|---|
| WO | 2005030049 A1 | 4/2005 |

OTHER PUBLICATIONS

Tai, Hideo; Tanaka, Hiroaki, "Fiber-optic evanescent-wave methane-gas sensor using optical absorption for the 3.392-micron line of a He-Ne laser", Optics Letters vol. 12, 6, pp. 4371987. (1987).

S. Thomas Lee*, R. Dinesh Kumar, P. Suresh Kumar, P. Radhakrishnan, C.P.G. Vallabhan, V.P.N. Nampoori "Long period gratings in multimode optical fibers: application in chemical sensing" (2003).

K. Postava, T. Yamaguchi, "Characterization of organiclow-dielectric-constant materials using optical spectroscopy", Optics Express vol. 9, No. 3, pp. 141 (2001).

Liu, Jia-Ming, Photonic Devices, Cambridge University Press, 2005.

* cited by examiner

FIG. 4A
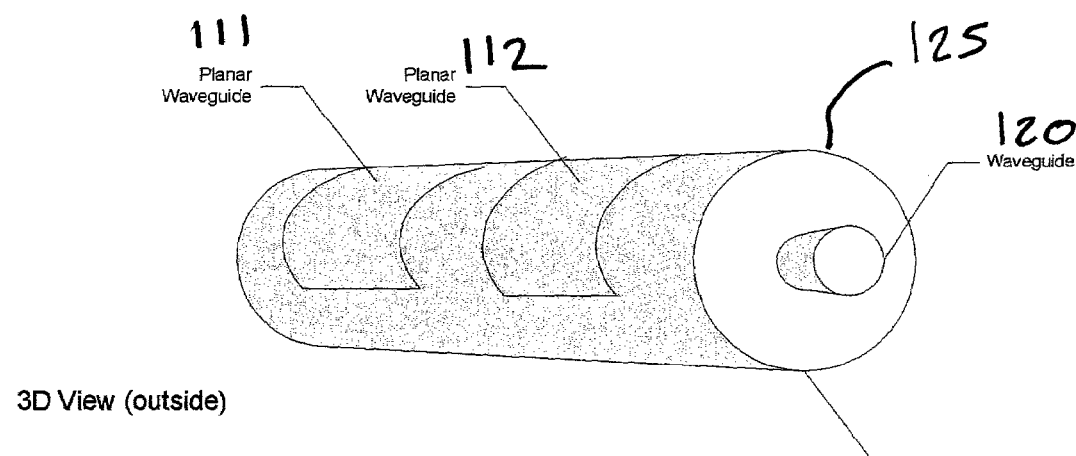
3D View (outside)
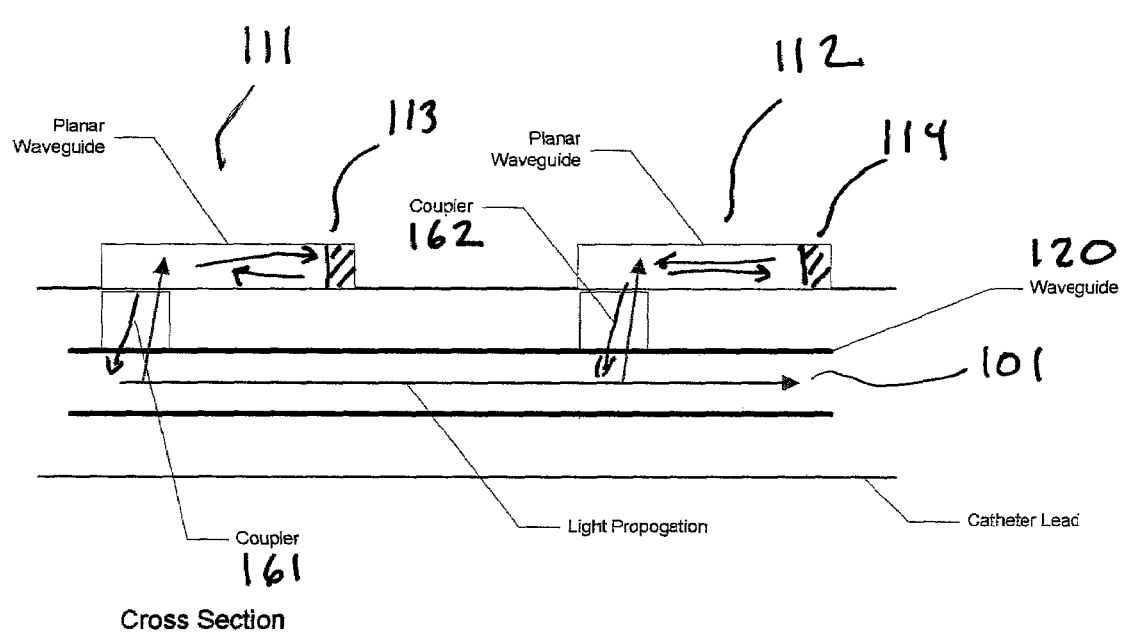
Cross Section
FIG. 4B

OPTICAL SENSING CATHETER SYSTEM

CROSS REFERENCE TO RELATED APPLICATIONS

The present application also claims priority to the U.S. provisional patent application for an "Optical Sensing Catheter System" filed Feb. 28, 2006, and assigned application Ser. No. 60/777,715, which is incorporated herein by reference.

The present application also claims priority to the U.S. provisional patent application for an "Optical and blood pressure and velocity sensor" filed on Feb. 28, 2006 and assigned application Ser. No. 60/777,727, which is incorporated herein by reference.

The present application also claims priority to the U.S. provisional patent application for an "Blood Oxygenation Sensor" filed Feb. 21, 2006, and assigned application Ser. No. 60/775,531, which is incorporated herein by reference.

BACKGROUND OF INVENTION

The present invention relates to method of simultaneous measurement of clinical blood parameters in an artery, vein or heart chamber, and in particular methods of making such measurements with optical transducers.

Catheters that include sensors to measure blood flow are well known. U.S. Pat. No. 5,280,786 to Wlodarczyk et al. issued on Jan. 25, 1994 for an Fiberoptic blood pressure and oxygenation sensor deployed on a catheter placed transcutaneously into a blood vessel. A sensing tip of the catheter includes a pressure-sensing element and an oxygen saturation-measuring element.

It is one object of the present invention to provide an improved method for utilizing a variety of optical transducers on the same or dispersed locations on a catheter or other implantable medical device to measure such parameters as blood flow or velocity, blood pressure, oxygenation of blood and the like.

SUMMARY OF INVENTION

In the present invention, the first object is achieved by providing a catheter or other medical device in optical communication with a plurality of optical sensors in communication with at least one light source and/or at least one photodetector wherein the plurality of detectors are responsive to or interrogated by a plurality of distinct wavelengths wherein a multiplexing scheme is used to distinguish among the different wavelength propagating in the common connecting optical waveguide and hence obtain analytical results from each detector.

The above and other objects, effects, features, and advantages of the present invention will become more apparent from the following description of the embodiments thereof taken in conjunction with the accompanying drawings.

BRIEF DESCRIPTION OF DRAWINGS

FIG. 4A is perspective view of an external portion of an optical sensing catheter system.

FIG. 4B is a cross-sectional elevation through the external portion of an optical sensing catheter system of FIG. 4A.

DETAILED DESCRIPTION

Figure 1:
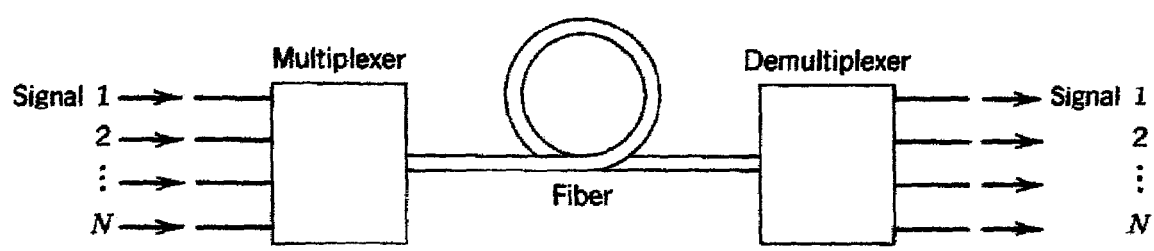
FIG. 1 is a schematic illustration of an optical wavelength divisional multiplexed/de-multiplexed (WDM) system.
Figure 2:
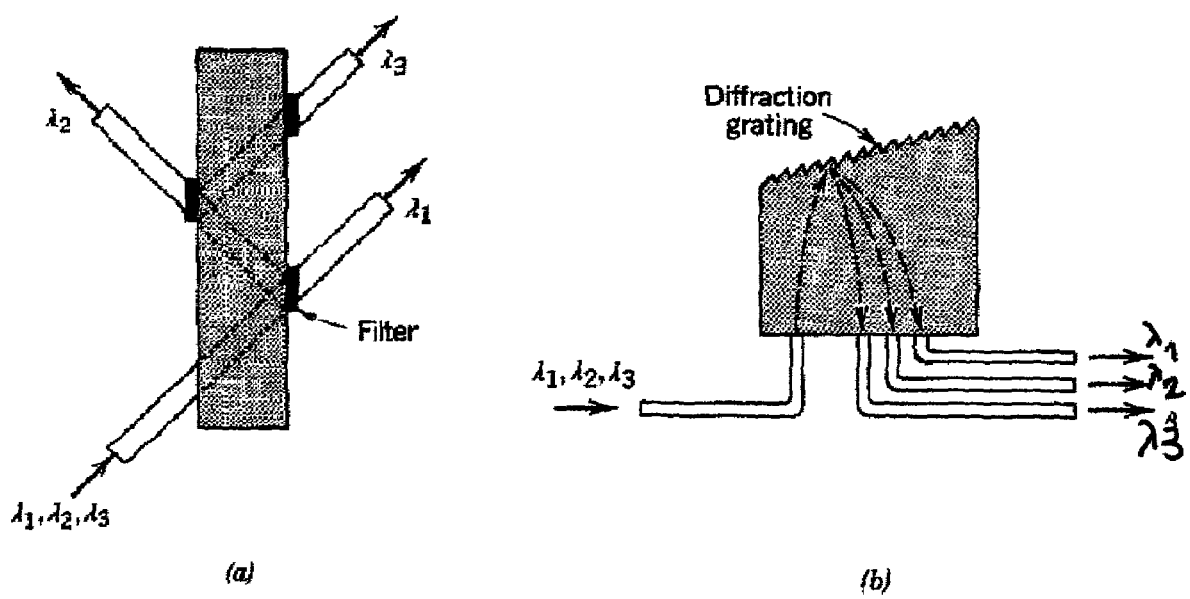
FIG. 2A is a schematic illustration of the operative principles of a first optical wavelength divisional de-multiplexer.
FIG. 2B is schematic illustration of the operative principles of a second optical wavelength divisional de-multiplexer.

Referring to FIGS. 1 through 4, wherein like reference numerals refer to like components in the various views, there is illustrated therein a new and improved Optical Sensing Catheter System, generally denominated 100 herein.

FIG. 1 illustrates the general operative principles of a communication system deploying wavelength division multiplexing (WDM). Wave Division Multiplexing (WDM) refers to a process of using light sources of different wavelengths with the intensity of each source being modulated to correspond to a different information as a temporal signal. The modulated light beams are then mixed into the fiber (or waveguide) using a set of optical couplers. The de-multiplexing of the signal is implemented at the receiver end utilizing optical filters, which separate the different wavelengths and direct them to different detectors (or sensors). Thus in the system shown in FIG. 1 N optical signals are simultaneously transmitted through the same fiber (or waveguide), being separately introduced or extracted with multiplexer and de-multiplexer respectively.

FIG. 2A illustrates an exemplary optical device used as a de-multiplexer.

These wave division de-multiplexers (WDDM) make use of optical filters to separate the different wavelengths and direct them to their respective detectors. Each of the dielectric interference filters transmits only a single wavelength and reflects other wavelengths. Also such filters may be based on selective absorption, preferably the filters electric thin-film interference filters such that substantially all the light not transmitted, and vice versa, is reflected and hence available for either detection of other wavelength or separation by another distinct filter. FIG. 2B illustrates another exemplary optical device used as a de-multiplexer wherein a diffraction grating separates the different wavelengths by angular dispersion, that is the light exits in different directions depending on the wavelength.

The ability to make multiple physiological and or heomological measurements at different locations with multiple sensors by WDM has several advantages.

It permits a small sensor and catheter size, thus avoiding interference with blood flow in smaller vessels. Further, the combined characterization of blood flow is useful in the diagnosis of vascular disease and the control of pacemakers and ICD's.

Figure 3:
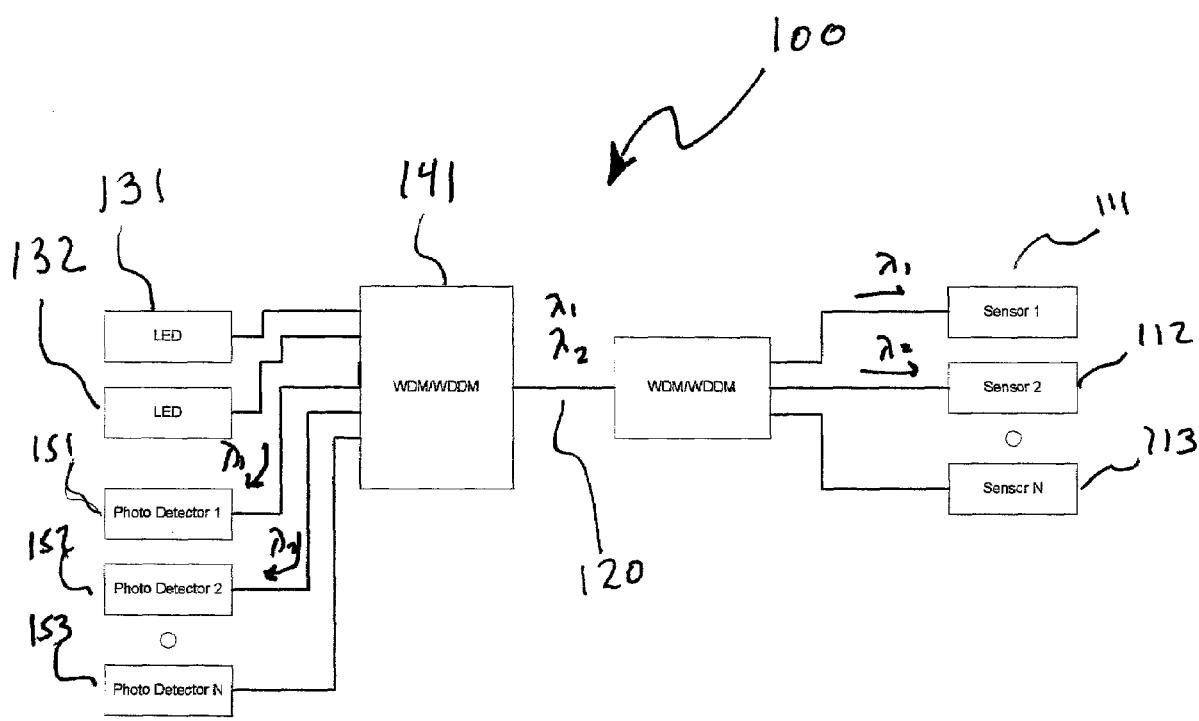
FIG. 3 is a block diagram of an optical sensing catheter system deploying WDM.

In accordance with the present invention, FIG. 3 is a block diagram showing the operative portion of the Optical Sensing Catheter System 100. In a preferred embodiment, each sensor 111, 112 or 113 can measure two or more of the parameters of blood gas (O2 for example), pressure and flow.

More preferably, the core of the device is a dielectric waveguide 120 have a sheath of ultimate exterior covering that is fabricated from a biocompatible material, wherein light at several specific wavelengths generated by using a light source, such as lasers or LEDs 131 and 132, is propagated through the waveguide 120 to specific areas where the waveguide is exposed to the environment, that is blood. For example, at the active portion of sensor elements 111, 112 and 113. The light source is optionally tunable LED's, or a fiber optic or pig-tailed laser.

As can be seen from FIG. 3, this device utilizes at least two LEDs 131 and 132 whose output light, represented as wavelengths λ1 and λ2 respectively, is passed through a first WDM 141 to co-propagate on the waveguide 120 to multiple sensors 111, 112 and 113 which perform the various measurements. After the interaction with blood in each sensor light is eventually de-multiplexed and propagated back along the waveguide where it is multiplexed back into N detectors. Optionally, a separate multiplexer 142 can operate as a de-multiplexer, by first directing specific wavelength λ1 to sensor 111, and a different wavelength λ2 to sensor 112, and then on the return (for example by reflection from a dielectric mirror at the end of sensor 111, 112 or 113) again multiplex the signal for redirection through waveguide 120 toward the photo-detectors. Thus, then multiplexer 141 acts as a de-multiplexer to select and direct light of specific wavelengths toward their respective photodetectors. Generally, each photodetector measures the intensity of light as attenuated by the interaction with blood in sensor 111, 112 or 113; however with other suitable means the photodetector may be responsive to measure a change in polarization or phase. In the case where it is desirable to measure at the same wavelength a blood parameter (such as the specific absorption wavelength that corresponds to a unique chemical species) with multiple sensors at different locations, time division multiplexing may be deployed wherein the apparatus includes fast optical switches to route the same wavelength to different chemical sensors.

Thus, device 100 allows for the usage of several sensors along the same waveguide 120, which will in turn allow for multiple blood gas, pressure and flow measurements-yielding information, which was not available in current state of the art in-vivo sensing systems.

FIG. 4A is perspective view of a more preferred embodiment of the invention as a portion of a medical device 100 in which the external portion of the optical sensors are planar waveguides 111 and 112. Planar waveguides are more sensitive due to their thin-wide structure. Planar optical sensors may be deployed for the measurement of blood chemistry, pressure, flow and/or temperature. Thus, in deploying an embodiment of the invention in a medical device, there is a sheath 125, an optical fiber (or waveguide) 120 protected by the sheath, at least one multi-wavelength light source, at least one multi-wavelength photo-detection means, two or more optical sensors in optical communication with the light source and photo-detection means wherein the optical sensors are in communication with the environment external to the sheath 125. Light propagates from the LEDs toward each sensor in the direction of the arrow 101 in waveguide 120.

Yet another import ant operative principle of an even more preferred embodiment of the current invention for measuring blood oxygen saturation level is to deploy a waveguide in which the dimensions of the evanescent field is comparable to, and most preferably, much more than the dimensions of the red blood cell. It should be appreciated that if the evanescent field that interacts with the RBC is much smaller than a RBC the signal will be strongly influenced by position of a particular red blood cell relative to the waveguide. The blood component hemoglobin is concentrated within erythrocytes or red blood cells that have a torus-like shape with the diameter of each corpuscular being is about 8 μm and having a thickness of about 2 μm. Further, the evanescent field should be of a nature that allows it to also penetrate deeply into the red blood cell. These two conditions are fulfilled for a low-dielectric constant (low-k) planar dielectric waveguide.

The spatial extension of evanescent field is proportional to $\lambda/\Delta n$, where $\Delta n$ is the difference of refractive index between the core and the cladding. The refractive index of the human red blood cells is in the range 1.38-1.42 depending on concentration of the hemoglobin in it. Therefore, the refractive index of the core of the waveguide should be as close to these values as possible to allow the evanescent light to penetrate deeply into the red blood cells. The refractive index of SiO2 waveguide is about 1.45. Thus, the typical penetration depth at that difference in refractive indexes between silica waveguide and red blood cell is 200-300 nm, or about between a tenth and a sixth of the thickness (2 μm)of the red blood cell. Accordingly, it is preferable that the waveguide 130 has a refractive index (n) is less than 1.45 at the absorption bands of oxygenated hemoglobin (Hb) and de-oxygenated hemoglobin ($HbO_2$). It is more preferable that the refractive index of the waveguide be in the range of about 1.375-about 1.45.

Thus, another embodiment of the invention is use of a dielectric material for waveguide with refractive index lower than that of silica to increase the penetration depth of the evanescent field, and thus obtain both a greater and more representative measurement of the blood oxygenation. One such preferred low-dielectric-constant material is spin-on hybrid siloxane-organic polymer, such as that known as HOSP and available from Honeywell Advanced Microelectronic Materials (Tempe, Ariz.). Thin films of HOSP could be prepared by a spin-on coating technique.

The sheath or the equivalent structure for supporting and introducing the optical device in the blood stream or body is optionally a cannula, catheter or medical devices in which the sensor is implanted on or communicates, such as pacemakers, ICD's and stents. In other preferred embodiments, the sheath 125 in FIGS. 4A and 4B is a catheter lead. This configuration is expected to offer advantages in the ease of manufacture, as it does not require significant changes in the lead itself, as only the external portion of the lead and the sensors need be exposed to the blood.

FIG. 4B is a cross-sectional elevation through the external portion of an optical sensing catheter system of FIG. 4A.

As can be seen from the image, this structure also utilizes several sensing areas on the lead itself. In contrast to the general scheme described with respect to FIG. 3, this device 100 uses corrugated waveguide couplers 161, 162 as both a coupler and multiplexer/de-multiplexer for each of the planar waveguides. It should be noted however, that any other type of waveguide coupler as is known in the art can be used instead of the corrugated waveguide couples 161 and 162. Each sensor 111 or 112 includes dielectric mirrors 113 and 114 respectively to reflect the modulated light back towards the coupler In alternative embodiments of the invention, it is possible to utilize multiple light sources, or replace one or more light source with a tunable light source, or utilize a broadband light source the output of which is separated into discrete measurements by optical filters. In other embodiments of the invention, light is returned to the photodetector either by a mirror means or via an optical loop.

It will be recognized by one of ordinary skill in the art that there are numerous alternative means to optically couple any of the contemplated or later developed optical transducers in optical communication with the laser and detector, such as for example means to provide the alternative forms of light coupling mean light is optionally returned to the photodetector either by a mirror means or via an optical loop. Additionally, a wide variety of multiplexing/de-multiplexing optical couplers are available as couplers. Accordingly, no attempt is being made to limit or define the invention in terms of the optical couplers shown and described with respect to FIGS. 2A and 2B.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

The invention claimed is:

1. An implantable medical device comprising:
   a) an elongated sheath,
   b) a waveguide disposed within said sheath,
   c) at least one multi-wavelength light source for illuminating said waveguide,
   d) at least one multi-wavelength photo-detection means to receive light from said waveguide,
   e) two or more optical sensors in optical communication with said light source and photo-detection means via said waveguide wherein each sensor is operative to modulate the propagation of light of a different wavelength in said waveguide wherein at least one sensor is for measuring the concentration of oxygenated and deoxygenated hemoglobin by direct contact with blood and comprises:
      i) a sensor waveguide having a planar support as a cladding on a first surface with a second surface parallel to the plane of the first surface and capable of being exposed directly to a fluid,
      ii) a reflective surface orthogonal to the direction of propagation of light within the sensor waveguide.

2. A device according to claim 1 wherein the evanescent light exiting the sensor waveguide is capable of substantially penetrating into red blood cells.

3. A device according to claim 1 wherein the sensor waveguide has a refractive index (n) that is less than 1.45 at the absorption bands of Hb and $HbO_2$.

4. A device according to claim 1 wherein the sensor waveguide has a refractive index (n) that is between about 1.375 and about 1.45 at the absorption bands of Hb and $HbO_2$.

5. A device according to claim 1 wherein said multi-wavelength light source is a pig-tailed laser.

6. A device according to claim 5 wherein said sheath is a catheter lead.

7. A device according to claim 1 wherein said sheath is a catheter lead.

8. A device according to claim 7 wherein said multi-wavelength light source is a pig-tailed laser.

9. An implantable medical device comprising:
   a) an elongated sheath,
   b) a waveguide disposed within said sheath,
   c) at least one multi-wavelength light source for illuminating said waveguide,
   d) at least one multi-wavelength photo-detection means to receive light from said waveguide,
   e) one or more optical sensors in optical communication with said light source and photo-detection means via said waveguide wherein each sensor is operative to modulate the propagation of light of a different wavelength in said waveguide wherein at least one sensor is for measuring blood pressure and comprises at least one Mach-Zehnder Interferometer (MZI) in optical communication with said waveguide and is disposed with a single arm in tactile communication with the environment external to said sheath and further comprising another optical sensor for measuring the concentration of oxygenated and deoxygenated hemoglobin by direct contact with blood, which comprises:
      i) a sensor waveguide having a planar support as a cladding on a first surface with a second surface parallel to the plane of the first surface and capable of being exposed directly to a fluid,
      ii) a reflective surface orthogonal to the direction of propagation of light within the sensor waveguide.

10. A device according to claim 9 wherein the evanescent light exiting the sensor waveguide is capable of substantially penetrating into red blood cells.

11. A device according to claim 10 wherein said sheath is a catheter lead.

12. A device according to claim 9 wherein the sensor waveguide has a refractive index (n) that is less than 1.45 at the absorption bands of Hb and $HbO_2$.

13. A device according to claim 9 wherein the sensor waveguide has a refractive index (n) that is between about 1.375 and about 1.45 at the absorption bands of Hb and $HbO_2$.

14. A device according to claim 13 wherein said sheath is a catheter lead.

* * * * *